(12) United States Patent
Ito et al.

(10) Patent No.: US 11,452,438 B2
(45) Date of Patent: Sep. 27, 2022

(54) ENDOSCOPE

(71) Applicant: OLYMPUS CORPORATION, Tokyo (JP)

(72) Inventors: Yoshiaki Ito, Tokyo (JP); Hidetada Sueyasu, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 426 days.

(21) Appl. No.: 16/708,960

(22) Filed: Dec. 10, 2019

(65) Prior Publication Data

US 2020/0113426 A1 Apr. 16, 2020

Related U.S. Application Data

(63) Continuation of application No. PCT/JP2018/015770, filed on Apr. 16, 2018.

(30) Foreign Application Priority Data

Jun. 13, 2017 (JP) .............................. JP2017-116232

(51) Int. Cl.
  *A61B 1/12* (2006.01)
  *A61B 1/018* (2006.01)
  *B08B 9/032* (2006.01)

(52) U.S. Cl.
  CPC .............. *A61B 1/125* (2013.01); *A61B 1/018* (2013.01); *A61B 1/123* (2013.01); *B08B 9/0321* (2013.01); *B08B 2209/032* (2013.01)

(58) Field of Classification Search
  None
  See application file for complete search history.

(56) References Cited

U.S. PATENT DOCUMENTS 6,699,183 B1    3/2004  Wimmer
2010/0160897 A1*  6/2010  Ducharme .......... A61M 5/1409
                                                         604/82

FOREIGN PATENT DOCUMENTS

| JP | S58-58001 U | 4/1983 |
| JP | S59-38901 U | 3/1984 |
| JP | H09-187417 A | 7/1997 |

(Continued)

OTHER PUBLICATIONS

JPH105174A Espacenet translation, Endoscope, Hamazaki, 1998 (Year: 1998).*

(Continued)

*Primary Examiner* — Cristi J Tate-Sims
(74) *Attorney, Agent, or Firm* — Scully, Scott, Murphy & Presser, P.C.

(57) ABSTRACT

An endoscope includes: a long member that is connected to a direction changing portion provided in an insertion portion and enables the direction changing portion to move; a sliding member that includes a first contact portion that is brought into contact with an inner surface of a guide tube that allows insertion of the long member and a second contact portion that is brought into contact with the inner surface of the guide tube; a flow path that includes an opening portion formed in a direction that intersects a longitudinal axis of the sliding member such that a fluid flows into a clearance between the guide tube and the sliding member; and an operation member that causes the sliding member to move forward and backward relative to the guide tube.

9 Claims, 11 Drawing Sheets

(56) References Cited

FOREIGN PATENT DOCUMENTS

JP        H10-5174 A     1/1998
WO     00/13569 A1    3/2000

OTHER PUBLICATIONS

International Search Report dated Jul. 10, 2018 received in PCT/JP2018/015770.

* cited by examiner

ENDOSCOPE

CROSS REFERENCE TO RELATED APPLICATION

This application is a continuation application of PCT/JP2018/015770 filed on Apr. 16, 2018 and claims benefit of Japanese Application No. 2017-116232 filed in Japan on Jun. 13, 2017, the entire contents of which are incorporated herein by this reference.

BACKGROUND OF THE INVENTION

1. Field of the Invention

The present invention particularly relates to an endoscope that has a piston configured to move a wire forward and backward.

2. Description of the Related Art

In related art, endoscopes capable of observing body cavity organs and the like by inserting an elongated insertion portion into a body cavity have been widely used in the medical field. In a case in which a monitor is caused to display an observation image of a body cavity organ or the like, an endoscope or the like with a solid state image pickup device such as a charge coupled device (CCD) disposed in an image pickup portion at a distal end or a rear end of an endoscope insertion portion is used.

A signal outputted from the image pickup device provided in the endoscope is converted into a video signal by an image processing apparatus, which is an external device of the endoscope provided separately from an electronic endoscope, an external camera, and the like, and is then outputted to a monitor. The electronic endoscope and the image processing apparatus that are configured separately are connected to each other via a connector for the endoscope.

International Publication No. 2000-013569A1, for example, discloses such an endoscope. In this publication, a technology is disclosed in which a side-viewing endoscope has a piston that is operated by an operation portion so as to project or be depressed, and by moving a wire connected to the piston forward and backward, a raising base provided at a distal end portion of an insertion portion is raised.

SUMMARY OF THE INVENTION

An endoscope according to an aspect of the invention includes: an insertion portion configured to be inserted into an object of examination from a distal end side in a longitudinal axis direction; a raising base that is provided at a distal end part of the insertion portion; a wire that is connected to the raising base and enables the raising base to move through traction and relaxation; a guide tube that allows insertion of the wire; a piston that is inserted into the guide tube and is connectable to the wire; a contact surface that is provided on a distal end side of the piston and is formed so as to project in an outer circumferential direction of the piston, such that the contact surface is brought into contact with an inner surface of the guide tube; a water-tight member that is provided on a proximal end side relative to the contact surface and is provided between the guide tube and the piston; a clearance that is defined by the inner surface of the guide tube and an outer circumferential surface of the piston, a flow path that is provided in the piston and includes a first flow path that is provided inside the piston along the longitudinal axis and causes a fluid for cleaning inside of the guide tube to be distributed, a second flow path that communicates with a distal end side of the first flow path and extends in a direction that intersects a longitudinal axis of the piston, and an opening portion that is formed at an end portion of the second flow path between the contact surface and the water-tight member such that the fluid flows into the clearance; and an operation member that causes the piston to move forward and backward relative to the guide tube.

DETAILED DESCRIPTION OF THE PREFERRED EMBODIMENTS

Here, an endoscope according to an aspect will be described as an example. In the following description, drawings based on the respective embodiments are for schematic illustration, and it should be noted that relationships between thicknesses and widths of the respective parts, thickness ratios of the respective parts, and the like are different from those in practice. There may be cases in which parts with dimensional relationships or ratios that are different from each other across the drawings may be included.

Although a so-called flexible endoscope that includes a flexible insertion portion to be inserted into a digestive organ on an upper or lower part of a living body will be exemplified to explain the endoscope in the following configuration description, the disclosure is not limited to the flexible endoscope and discloses a technology that can also be applied to a so-called rigid endoscope with a rigid insertion portion that is used for surgical purposes.

First Embodiment

Hereinafter, an endoscope according to an aspect of the invention will be described on the basis of drawings.

Figure 1:
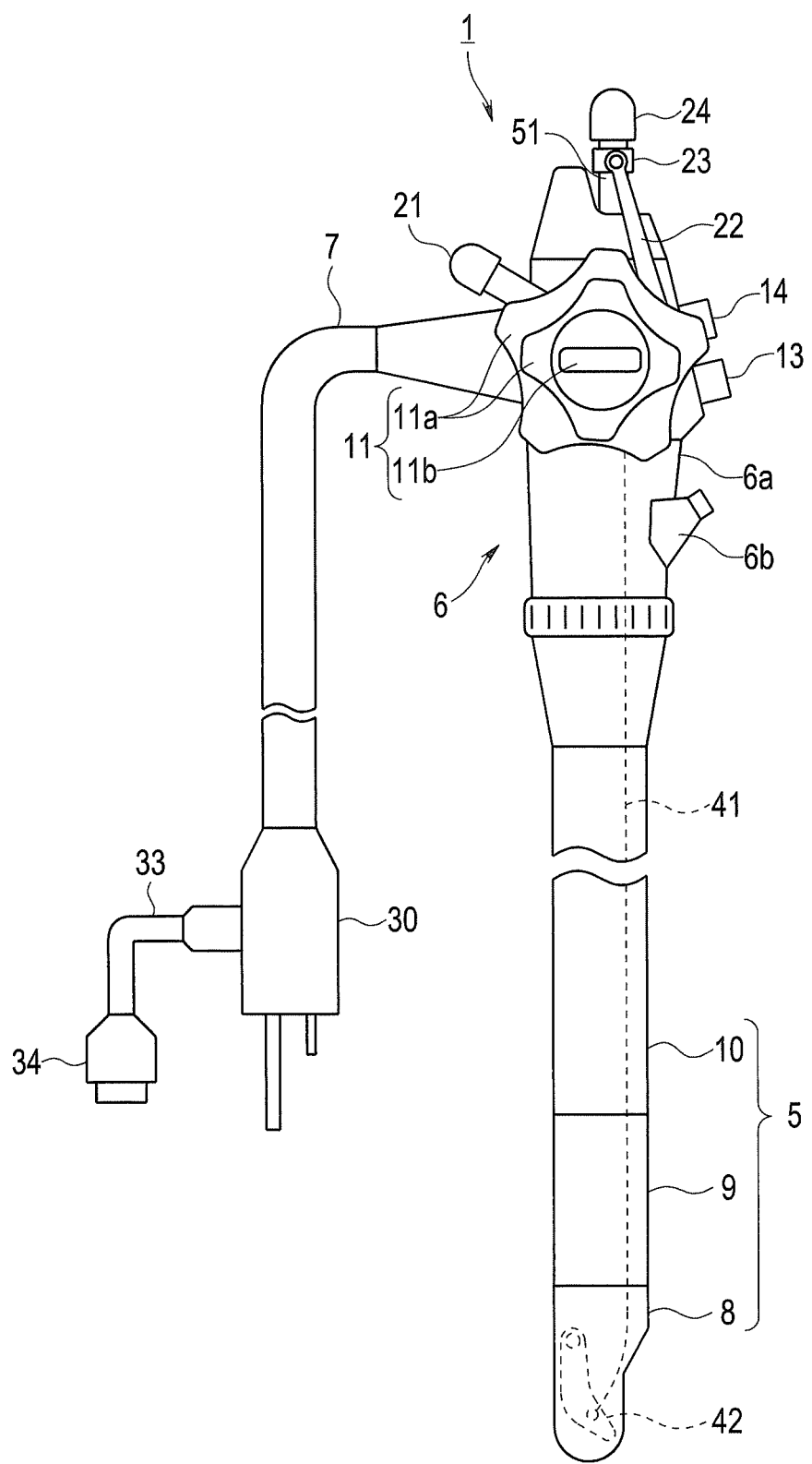
FIG. 1 is a side view illustrating a configuration of an endoscope according to a first embodiment.
Figure 2:
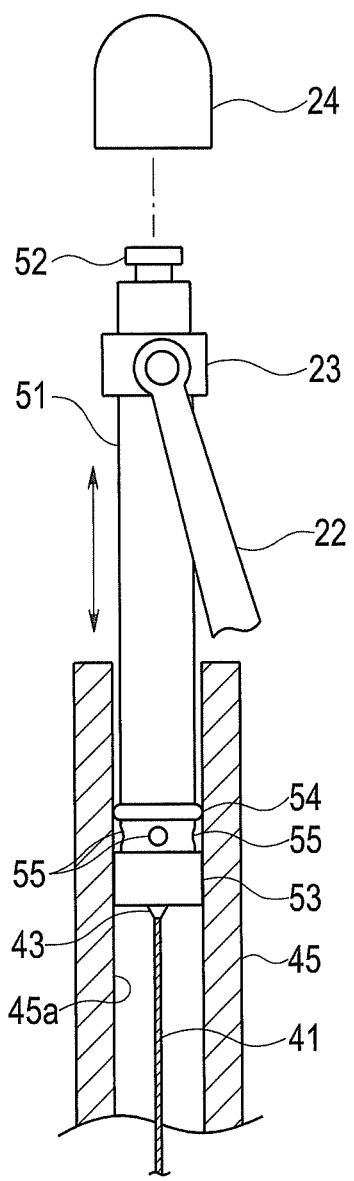
FIG. 2 is a partial sectional view mainly illustrating configurations of a cylinder and a piston according to the first embodiment.
Figure 3:
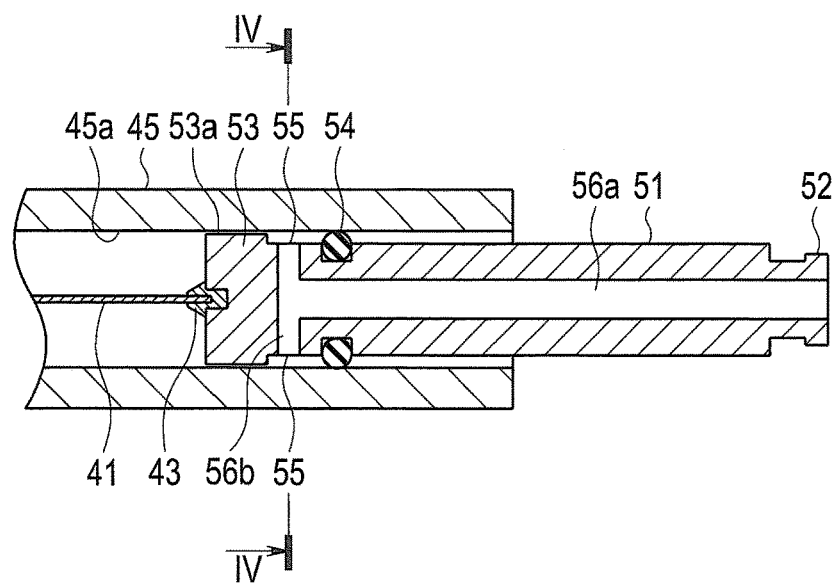
FIG. 3 is a sectional view illustrating a configuration of the piston inserted into the cylinder according to the first embodiment.
Figure 4:
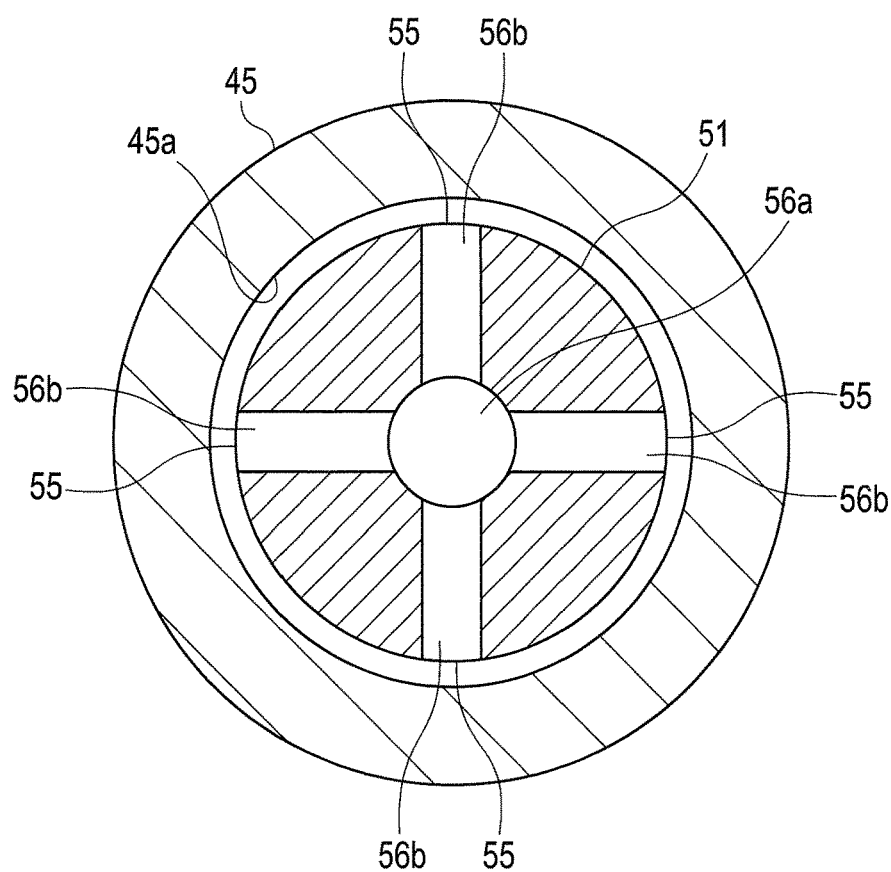
FIG. 4 is a sectional view taken along the line IV-IV in FIG. 3 according to the first embodiment.
Figure 5:
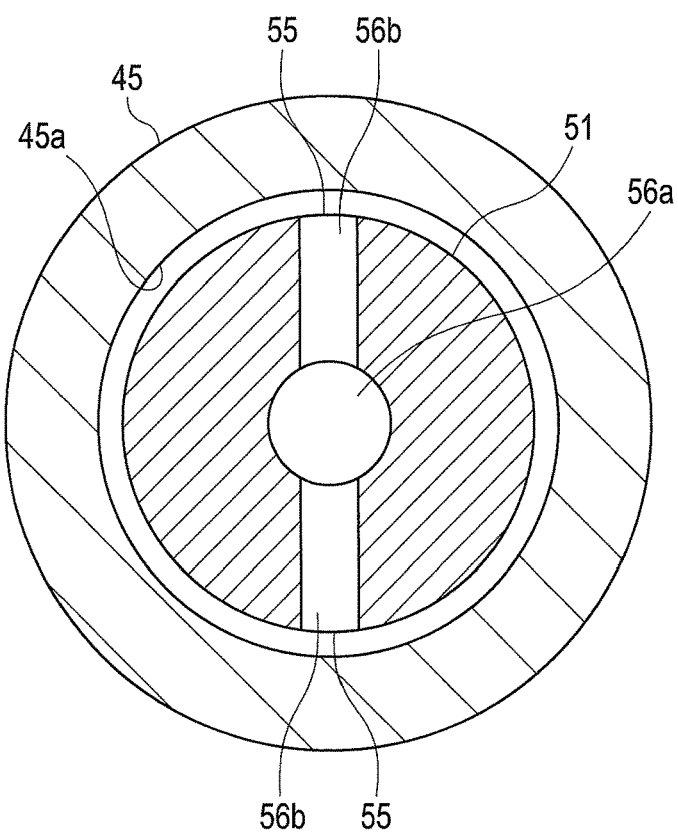
FIG. 5 is a sectional view illustrating a configuration in which the number of communication paths that communicate with a channel of the piston inserted into the cylinder is two according to the first embodiment.
Figure 6:
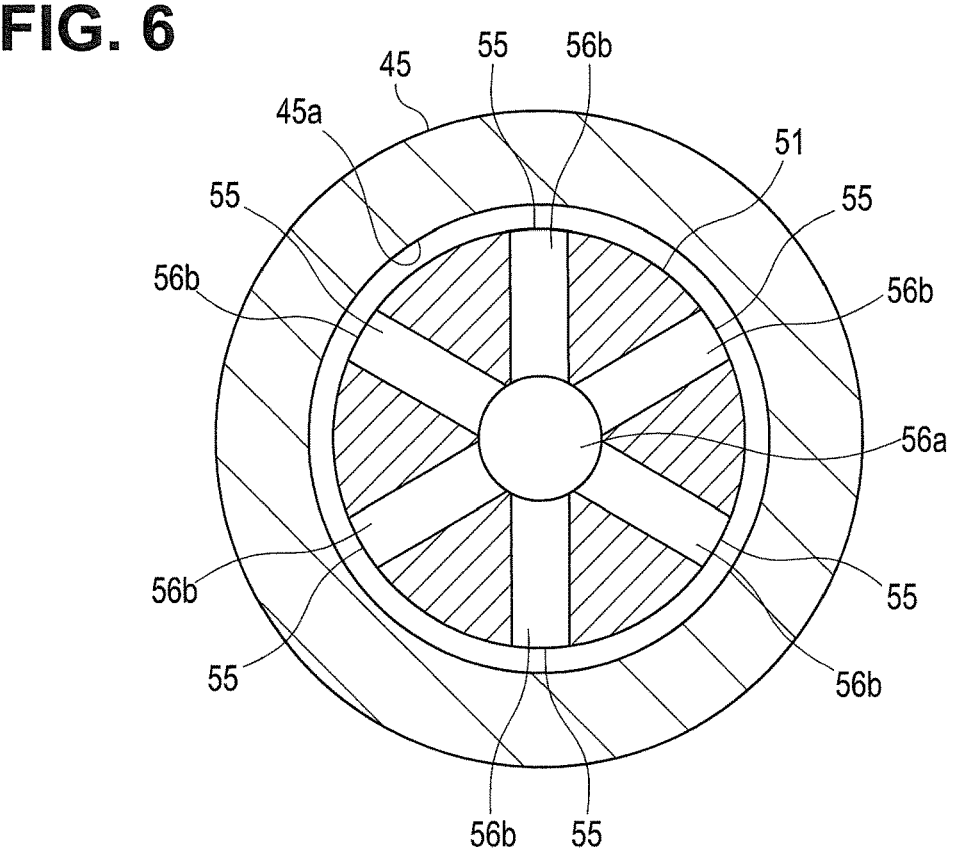
FIG. 6 is a sectional view illustrating a configuration in which the number of communication paths that communicate with the channel of the piston inserted into the cylinder is six according to the first embodiment.
Figure 7:
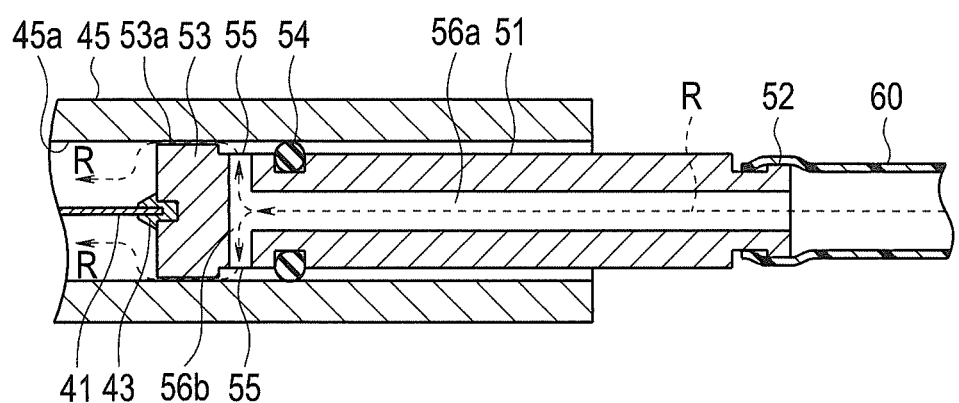
FIG. 7 is a sectional view illustrating a state in which a cleaning solution has been fed to the channel of the piston according to the first embodiment.

FIG. 1 is a side view illustrating a configuration of the endoscope, FIG. 2 is a partial sectional view mainly illustrating configurations of a cylinder and a piston, FIG. 3 is a sectional view illustrating a configuration of the piston inserted into the cylinder, FIG. 4 is a sectional view taken along the line IV-IV in FIG. 3, FIG. 5 is a sectional view illustrating a configuration in which the number of communication paths that communicate with a channel of the piston inserted into the cylinder is two, FIG. 6 is a sectional view illustrating a configuration in which the number of communication paths that communicate with the channel of the piston inserted into the cylinder is six, and FIG. 7 is a sectional view illustrating a state in which a cleaning solution has been fed to the channel of the piston.

An endoscope 1 according to the embodiment has an insertion portion 5, an operation portion 6, and a universal cable 7. The insertion portion 5 is an elongated, long member that is inserted into an observation target site from a distal end side in a longitudinal axis direction. The insertion portion 5 is configured such that a distal end portion 8, a bending portion 9, and a flexible tube portion 10 are sequentially provided.

The distal end portion 8 incorporates an illumination optical system provided with a light guide and an image pickup optical system provided with an image pickup apparatus, and a suctioning port that serves both as a nozzle and a treatment instrument outlet is provided in a distal end surface (both are not illustrated in the drawings).

At the distal end portion 8, an observation window and an illumination window are provided at predetermined angles with respect to an insertion direction of the insertion portion 5, and a raising base 42 that serves as a direction changing portion that raises a treatment instrument to change the direction of the treatment instrument in an observation direction is disposed.

The raising base 42 is connected to a wire 41 that is an elongated member to be inserted into the insertion portion 5 and the operation portion 6. An operation of raising the raising base 42 is performed through traction and relaxation of the wire 41.

The bending portion 9 is configured so as to be freely bent in four directions, namely upward, downward, leftward, and rightward, for example. The flexible tube portion 10 is a tubular member that is elongated and has flexibility.

The operation portion 6 includes a grasping portion 6a, the grasping portion 6a is provided continuously from a proximal end portion of the insertion portion 5, and a treatment instrument insertion port 6b is disposed.

The operation portion 6 is provided with a bending operation portion 11, an air/water feeding button 13, a suctioning button 14, and the like. The operation portion 6 is provided with a raising base operation lever 21 that serves as an operation member, and a piston 51 that serves as a direction changing mechanism portion projects and is depressed (moves forward and backward) by a linking member 22 that serves as an operation member that moves in conjunction with an operation of the raising base operation lever 21. The piston 51 will be described later in detail.

The bending operation portion 11 includes a bending operation knob 11a for performing a bending operation on the bending portion 9 and a fixation lever 11b for fixing the bending operation knob 11a at a desired rotation position.

A universal cable 7 extends from a side surface of the operation portion 6. An endoscope connector 30 to be connected to a light source device, which is an external device, is provided at an end portion of the universal cable 7. The endoscope connector 30 includes a signal transmission cable 33 extending from a side portion of the endoscope connector 30. The signal transmission cable 33 includes, on the other end side of the signal transmission cable 33, an electrical connector 34 to be connected to a video processor.

The piston 51 that serves as a sliding member here is inserted into a cylinder 45 that serves as a guide tube as illustrated in FIG. 2. A holding ring 23 with an end portion of the linking member 22 turnably provided is secured to an intermediate portion of the piston 51 on a proximal end side.

A connecting end portion 52 with a small diameter with a circumferential groove formed in the connecting end portion 52 is provided on a proximal end side of the piston 51 in the longitudinal axis direction, and a detachable cap 24 for sealing the connecting end portion 52 is disposed through screwing or the like. A wire connecting portion 43 is provided at the center of the distal end of the piston 51 through pressure-fitting, screwing, or the like, and the wire 41 with an end portion fixed to and held by the wire connecting portion 43 is inserted into the cylinder 45 toward the distal end side.

Here, the piston 51 and the cylinder 45 to which the wire 41 is connected configure the direction changing mechanism portion that raises the raising base 42 to change the direction of the treatment instrument.

The piston 51 includes, at a distal end part of the piston 51, a sliding portion 53 that serves as a first contact portion, is brought into contact with and slides along an inner surface 45a of the cylinder 45, and is formed so as to project in an outer circumferential direction, an O-shaped ring 54 that serves as a second contact portion disposed on the proximal end side relative to the sliding portion 53 in the longitudinal axis direction and performs sealing as a water-tight member, and a plurality of, in this case, four opening portions 55 formed in a direction that intersects the longitudinal axis of the piston 51.

A sliding surface 53*a*, which is an outer circumferential surface, of the sliding portion 53 is substantially in surface contact with the inner surface 45*a* of the cylinder 45 as illustrated in FIG. 3 and is guided so as to advance straight relative to the cylinder 45 when the piston 51 moves forward and backward. The O-shaped ring 54 is in close contact with the inner surface 45*a* of the cylinder 45 and seals an inside of the cylinder 45 on the distal end side in a water-tight manner.

The four opening portions 55 are the respective openings of four communication paths 56*b* that communicate with a channel 56*a* that serves as a flow path formed inside the piston 51 that serves as a flow path here along a central axis of the piston 51 and that serve as flow paths penetrated radially at equal intervals at 90 degrees around the center of the piston 51, and the four opening portions 55 are formed in the outer circumferential surface of the piston 51 between the sliding portion 53 and the O-shaped ring 54 as illustrated in FIG. 4. In other words, the piston 51 is a tubular member that includes the channel 56*a* and the four communication paths 56*b*.

The communication paths 56*b* may be configured such that two communication paths 56*b* are formed at positions at equal intervals (symmetric about the center point) at 180 degrees around the center of the piston 51 and two opening portions 55 are provided as illustrated in FIG. 5, or the communication paths 56*b* may be configured such that six communication paths 56*b* are radially formed at equal intervals at 60 degrees and six opening portions 55 are provided as illustrated in FIG. 6. Alternatively, one communication path 56*b* and one opening portion 55 may be provided, or the communication paths 56*b* and the opening portions 55 may not necessarily be provided at equal intervals around the center of the piston 51.

A tube 60 is connected to a connecting end portion 52 of the piston 51 configured in this manner as illustrated in FIG. 7 when the endoscope 1 is cleaned, and a syringe, which is not illustrated in the drawings, supplies a cleaning solution R that is a fluid for cleaning the inside and the like of the cylinder 45 to the inside of the channel 56*a*.

The cleaning solution R supplied to the inside of the channel 56*a* flows to the four communication paths 56*b* and flows out of the respective opening portions 55 to the outer circumferential portion of the piston 51.

A flow of the cleaning solution R, which has flow out, toward the proximal end side is stopped with the O-shaped ring 54, and the cleaning solution R enters a gap between the sliding portion 53 on the distal end side and the inner surface 45*a* of the cylinder 45 due to a supply pressure caused by the syringe. Then, the cleaning solution R flows into the cylinder 45 on the distal end side relative to the piston 51 while cleaning the entire sliding surface 53*a* of the sliding portion 53 from the proximal end side toward the distal end side.

In this manner, according to the embodiment, it is possible to keep a small clearance between the sliding surface 53*a* of the sliding portion 53 and the inner surface 45*a* of the cylinder 45 such that no backlash of the piston 51 occurs and to clean the clearance by causing the cleaning solution R to pass between the inner surface 45*a* and the sliding surface 53*a* of the sliding portion 53 even if the clearance is small.

Causing the piston 51 to move forward and backward while feeding the cleaning solution R further enhances cleaning properties. Therefore, there is no need to repeatedly feed the cleaning solution R, and the cleaning operation does not become complicated and can be easily performed.

As described above, the endoscope 1 according to the embodiment can be configured such that the sliding portion 53 of the piston 51, which slides along the cylinder 45, can be easily cleaned.

(Modification)

Figure 8:
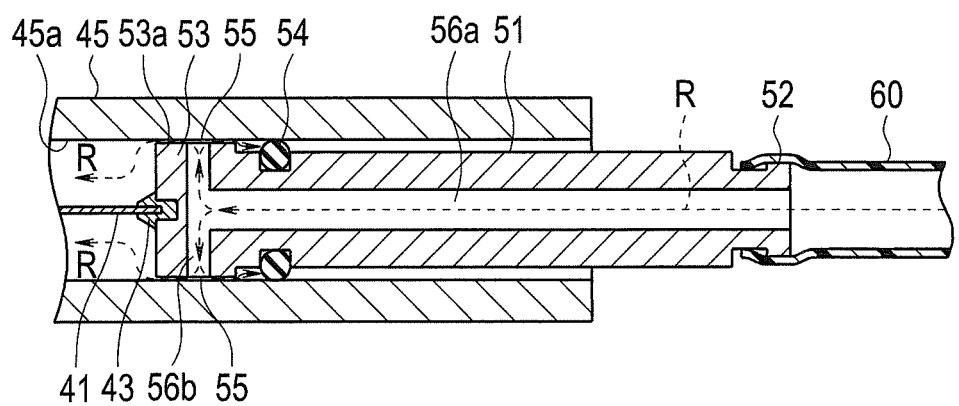
FIG. 8 is a sectional view illustrating a configuration of a piston inserted into a cylinder according to a modification of the first embodiment.

FIG. 8 is a sectional view illustrating a configuration of a piston inserted into a cylinder according to a modification.

As illustrated in FIG. 8, the communication paths 56*b* may be formed such that the opening portions 55 are formed in the sliding surface 53*a* of the sliding portion 53 of the piston 51, that is, between an end portion of the sliding portion 53, which is the first contact portion, and the O-shaped ring 54, which is the second contact portion. Also, the number of the communication paths 56*b* and the number of the opening portions 55 formed in the sliding surface 53*a* described herein may be four, two, six, one, or the like and are not limited as described above.

Second Embodiment

Next, a configuration of a second embodiment will be described. In description of the embodiment, the same reference numerals will be used for components that are the same as the components in the aforementioned first embodiment, and detailed description of the components will be omitted.

Figure 9:
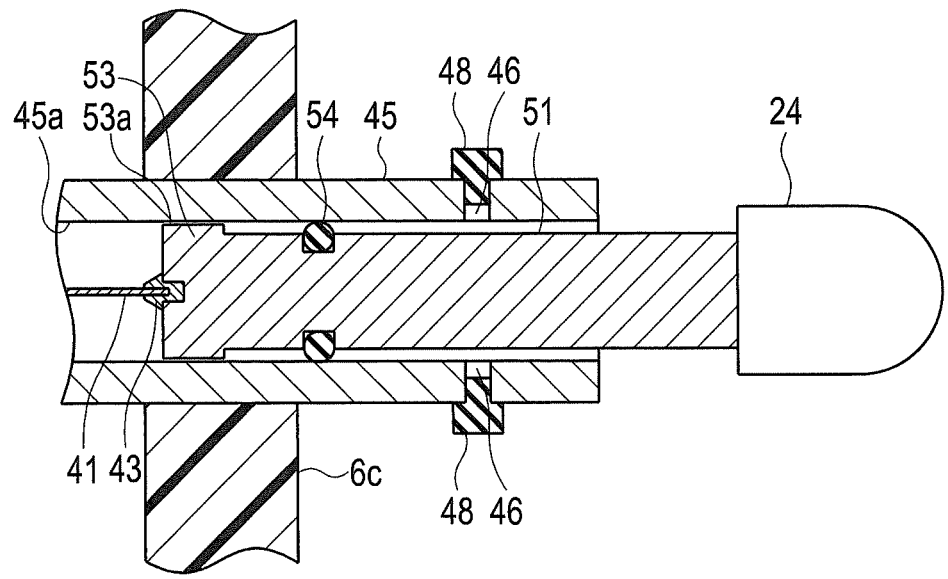
FIG. 9 is a sectional view illustrating a configuration of a piston inserted into a cylinder according to a second embodiment.
Figure 10:
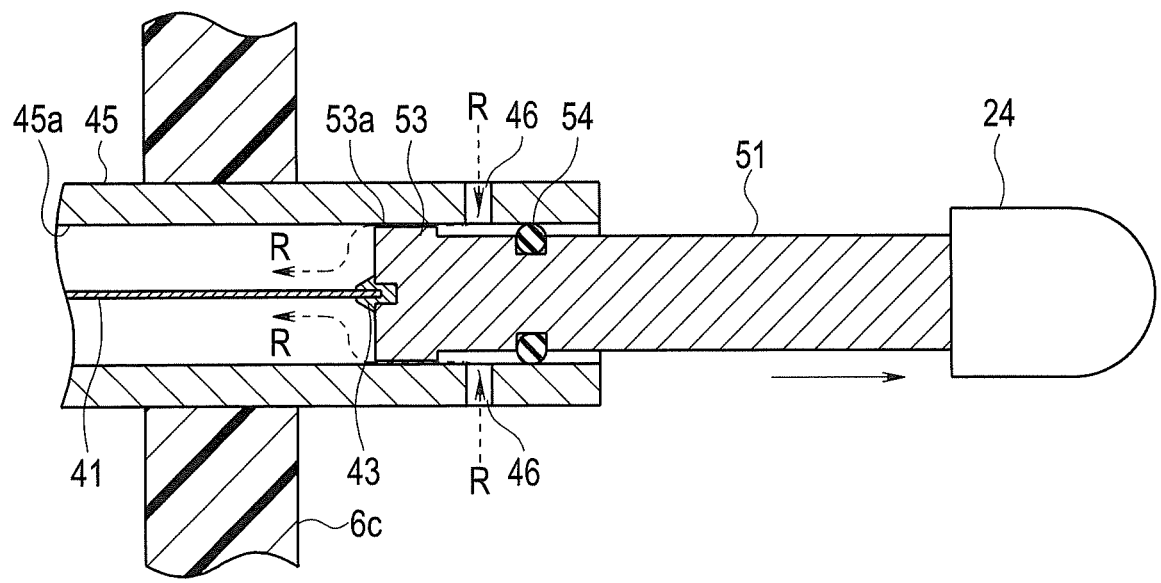
FIG. 10 is a sectional view illustrating a state in which a cleaning solution has been fed to the cylinder according to the second embodiment.

FIG. 9 is a sectional view illustrating a configuration of a piston inserted into a cylinder according to the second embodiment, and FIG. 10 is a sectional view illustrating a state in which a cleaning solution has been fed to the cylinder.

As illustrated in FIG. 9, a piston 51 described herein has, for example, a substantially columnar solid shape with neither the channel 56*a* nor the communication paths 56*b* described in the first embodiment.

Then, the piston 51 has a sliding portion 53 that has a sliding surface 53*a* at a distal end and serves as a first contact portion, and an O-shaped ring 54 that serves as a second contact portion is provided at an intermediate portion of the piston 51 in the vicinity of the sliding portion 53, that is, at a predetermined distance from the sliding portion 53 on a proximal end side in the longitudinal axis direction relative to the sliding portion 53.

In the cylinder 45, a plurality of, in this case, two communication holes 46 that serve as flow paths for feeding a cleaning solution R to outside of an operation portion 6, which is outside of an exterior portion 6*c* of the operation portion 6, are formed from a side portion side toward an inner portion. These communication holes 46 are sealed with valve bodies 48 that are water-tight members such as rubber stoppers and that serve as stopper members.

The piston 51 is moved to the proximal end side such that the communication holes 46 of the cylinder 45 are located between the sliding portion 53 and the O-shaped ring 54 as illustrated in FIG. 10. In other words, the piston 51 is moved such that the sliding portion 53 is located on the distal end side relative to the communication holes 46 and the O-shaped ring 54 is located on the proximal end side relative to the communication holes 46.

Then, the valve bodies 48 are removed from the communication holes 46, and a syringe, which is not illustrated in the drawings, feeds the cleaning solution R from the communication holes 46. The O-shaped ring 54 stops a flow of the cleaning solution R, which has flown into the cylinder 45, toward the proximal end side, and the cleaning solution R enters a gap between the sliding portion 53 on the distal end side and an inner surface 45a of the cylinder 45 due to a supply pressure applied by the syringe in this case as well.

The cleaning solution R flows into the cylinder 45 on the distal end side relative to the piston 51 while cleaning the entire sliding surface 53a of the sliding portion 53 from the proximal end side toward the distal end side. The other components and effects are the same as the components and effects in the first embodiment.

This configuration can be a configuration that achieves similar effects and advantages to the effects and advantages in the first embodiment and can provide the endoscope 1 that enables easy cleaning of the sliding portion 53 of the piston 51, which slides along the cylinder 45.

It is also possible to employ a configuration with no need to provide the valve bodies 48 at the communication holes 46 by defining a movable range of the piston 51 when the endoscope 1 is used. In other words, there is no need to provide the valve bodies 48 at the communication holes 46 if a range, in which the O-shaped ring 54 moves forward and backward, which is provided at the piston 51, is on the distal end side relative to the communication holes 46 in the movable range of the piston 51 when the endoscope 1 is used.

(First Modification)

Figure 11:
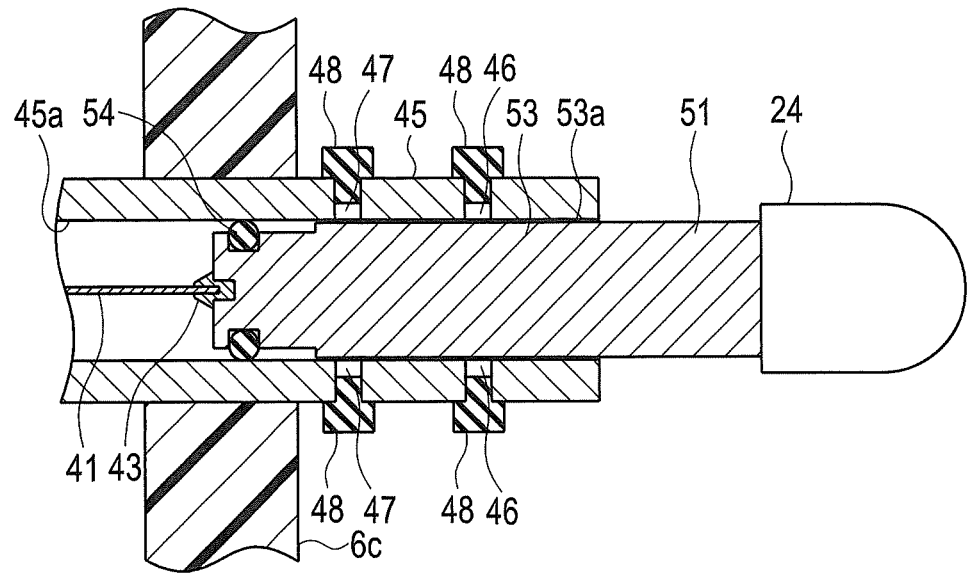
FIG. 11 is a sectional view illustrating a configuration of a piston inserted into a cylinder according to a first modification of the second embodiment.
Figure 12:
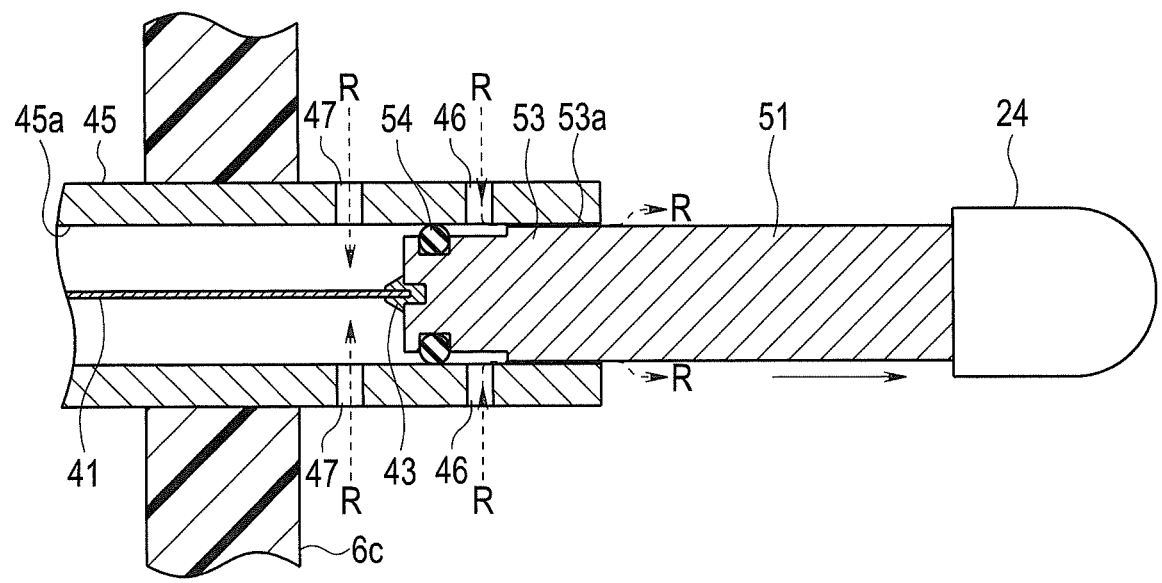
FIG. 12 is a sectional view illustrating a state in which a cleaning solution has been fed to the cylinder according to the first modification of the second embodiment.
Figure 13:
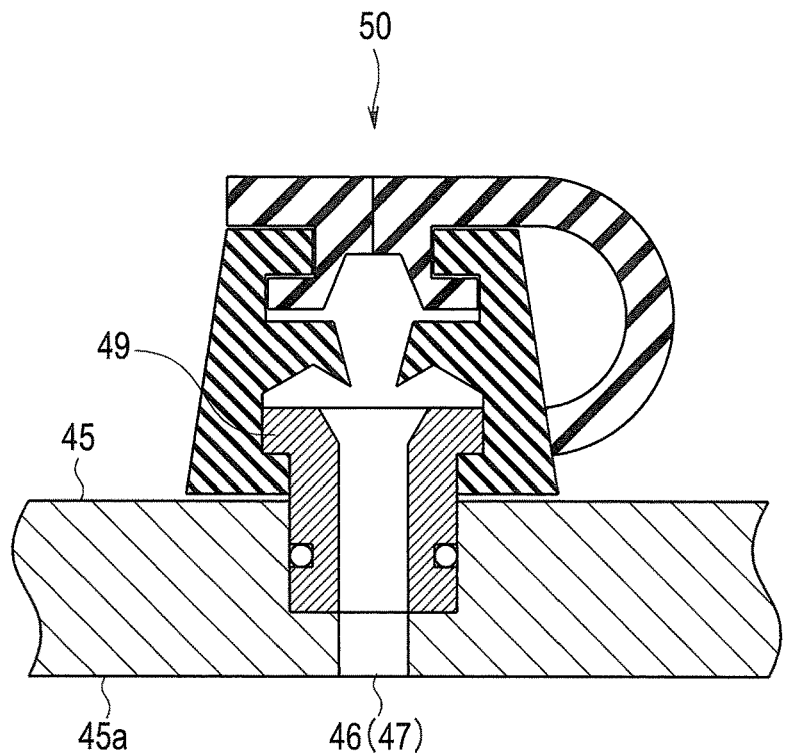
FIG. 13 is a sectional view illustrating a configuration in which a pipe sleeve is provided at a communication hole and a stopper member is disposed according to the second embodiment.
Figure 14:
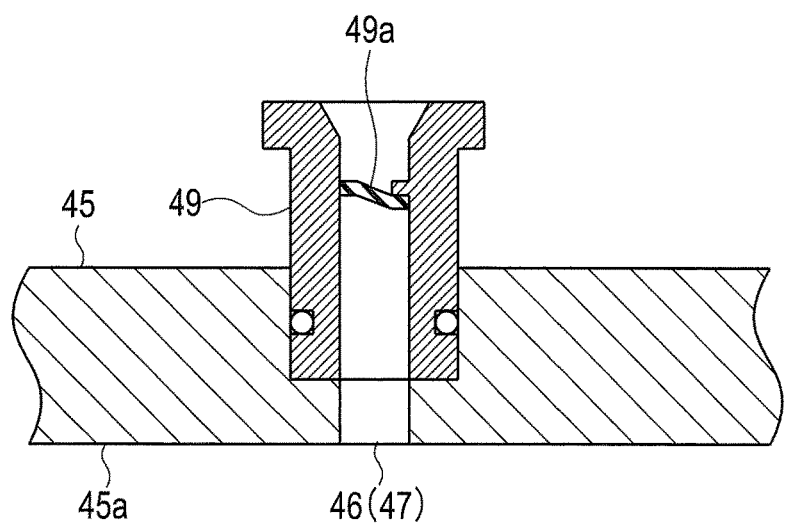
FIG. 14 is a sectional view illustrating a configuration in which a pipe sleeve with a check valve is provided at the communication hole according to the second embodiment.

FIG. 11 is a sectional view illustrating a configuration of a piston inserted into a cylinder according to a first modification, FIG. 12 is a sectional view illustrating a state in which a cleaning solution has been fed to the cylinder according to the first modification, FIG. 13 is a sectional view illustrating a configuration in which a pipe sleeve is provided at a communication hole and a valve body is disposed, and FIG. 14 is a sectional view illustrating a configuration in which a pipe sleeve with a check valve is provided at the communication hole.

As illustrated in FIG. 11, a plurality of, in this case, a total of four communication holes 46 and 47 are formed from the side portion side toward the inner portion of the cylinder 45 described herein along the longitudinal axis outside the operation portion 6, which is outside the exterior portion 6c of the operation portion 6.

These communication holes 46 and 47 are sealed with the valve bodies 48 that are water-tight members such as rubber stoppers and that serve as stopper members. Note that the communication holes 46 on the proximal end side and the communication holes 47 on the distal end side are formed at positions separated at a predetermined distance along the longitudinal axis of the cylinder 45.

The piston 51 described herein includes an O-shaped ring 54 that is provided at a distal end part (on the distal end side in the longitudinal axis direction) as a first contact portion and that slides in contact with the inner surface 45a of the cylinder 45, and the piston 51 has a sliding portion 53 that is provided at a predetermined distance from the O-shaped ring 54 and that has a sliding surface 53a that serves as a second contact portion sliding in contact with the inner surface 45a of the cylinder 45 toward the proximal end side in the longitudinal axis direction.

The piston 51 is moved to the proximal end side such that the communication holes 46 of the cylinder 45 are located between an end portion of the sliding portion 53 and the O-shaped ring 54 as illustrated in FIG. 12. The piston 51 is moved such that the sliding portion 53 is located on the proximal end side relative to the communication holes 46 and the O-shaped ring 54 is located on the distal end side relative to the communication holes 46 in this case as well.

Further, the piston 51 is moved such that the O-shaped ring 54 is located between the communication holes 46 and 47.

Then, the valve bodies 48 are removed from the communication holes 46 and 47, and the syringe, which is not illustrated in the drawings, feeds the cleaning solution R from the communication holes 46 and 47.

The O-shaped ring 54 stops a flow of the cleaning solution R, which has flown into the cylinder 45 from the communication holes 46 on the proximal end side, toward the distal end side, and the cleaning solution R enters a gap between the sliding portion 53 on the proximal end side and the inner surface 45a of the cylinder 45 due to a supply pressure caused by the syringe in this case as well. The cleaning solution R flows to the outside of the cylinder 45 while cleaning the entire sliding surface 53a of the sliding portion 53 from the distal end side toward the proximal end side.

The cleaning solution R that has flown into the cylinder 45 from the communication holes 47 on the distal end side flows to the distal end side of the cylinder 45. The other components and effects are the same as the components and effects in the first embodiment.

This configuration can also be a configuration that achieves similar effects and advantages to the effects and advantages in the first embodiment and can provide the endoscope 1 that enables easy cleaning of the sliding portion 53 of the piston 51, which slides along the cylinder 45.

Pipe sleeves 49 may be provided at the communication holes 46 (47) and valve bodies 50 that are stoppers made of rubber or the like so as to be freely opened and closed may be provided as illustrated in FIG. 13, or alternatively, pipe sleeves 49 with check valves 49a may be provided at the communication holes 46 (47) as illustrated in FIG. 14.

Third Embodiment

Next, a configuration according to a third embodiment will be described. The same reference numerals will be used for the same components as the components in the aforementioned first embodiment or second embodiment, and detailed description of the components will be omitted in the description of this embodiment as well.

Figure 15:
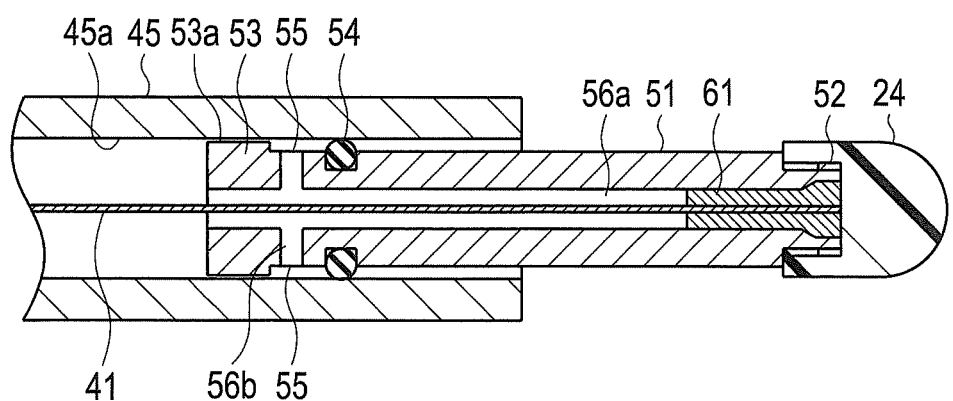
FIG. 15 is a sectional view illustrating a configuration of a piston inserted into a cylinder according to a third embodiment.
Figure 16:
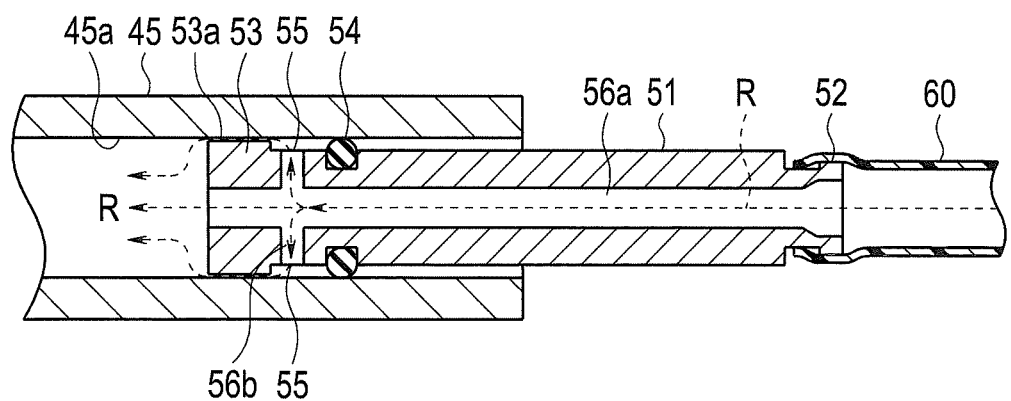
FIG. 16 is a sectional view illustrating a state in which a cleaning solution has been fed to the cylinder according to the third embodiment.

FIG. 15 is a sectional view illustrating a configuration of a piston inserted into a cylinder according to a third embodiment, and FIG. 16 is a sectional view illustrating a state in which a cleaning solution has been fed to the cylinder.

As illustrated in FIG. 15, a channel 56a formed as a flow path inside a piston 51 described herein along the central axis is a through-hole, and a wire 41 is inserted into the channel 56a.

A proximal end of the wire 41 is secured to a proximal end part of the piston 51 by being fastened with a cap using a collet chuck 61. The other components are the same as the components in the first embodiment.

As illustrated in FIG. 16, a cap 24 is removed, the collet chuck 61 is taken out of the piston 51, the wire 41 is pulled out from the distal end side, and a tube 60 is then connected to a connecting end portion 52 of the piston 51.

Then, a syringe, which is not illustrated in the drawings, supplies a cleaning solution R to a channel 56a. The cleaning solution R that has been supplied to the channel 56a flows to communication paths 56b and flows out of the respective opening portions 55 to an outer circumferential portion of the piston 51 similarly to the first embodiment. The cleaning solution R also flows from a distal end opening of the channel 56a into the cylinder 45.

Then, the cleaning solution R that has flown out of the respective opening portions 55 enters a gap between a sliding portion 53 on the distal end side and an inner surface 45a of the cylinder 45, the O-shaped ring 54 that serves as a second contact portion stops a flow of the cleaning solution R in a longitudinal axis proximal end direction, and the cleaning solution R thus flows into the cylinder 45 while cleaning the entire sliding surface 53a of the sliding portion 53 that serves as a contact portion. In this manner, it is possible to perform cleaning by causing the cleaning solution R to pass between the sliding surface 53a of the sliding portion 53 and the inner surface 45a of the cylinder 45 in this embodiment as well.

This configuration can also be a configuration that achieves similar effects and advantages to the effects and advantages in the first embodiment and can provide the endoscope 1 that enables easy cleaning of the sliding portion 53 of the piston 51, which slides along the cylinder 45.

(First Modification)

Figure 17:
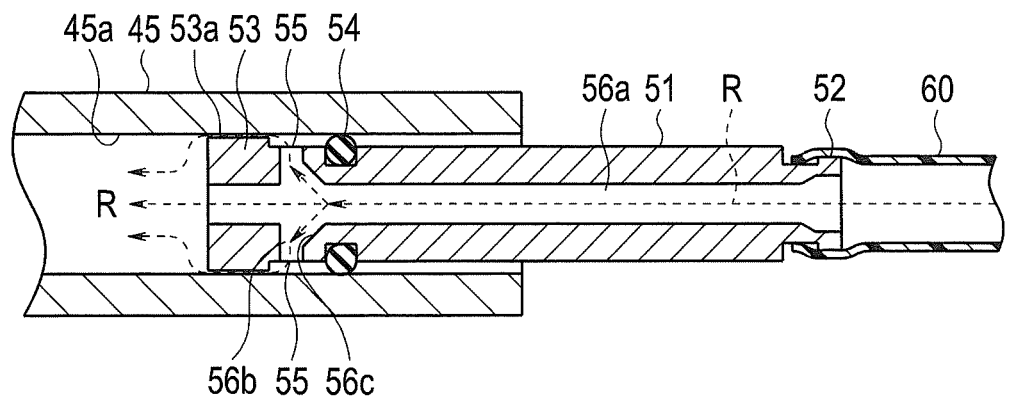
FIG. 17 is a sectional view illustrating a state in which a cleaning solution has been fed to a cylinder according to a first modification of the third embodiment.
Figure 18:
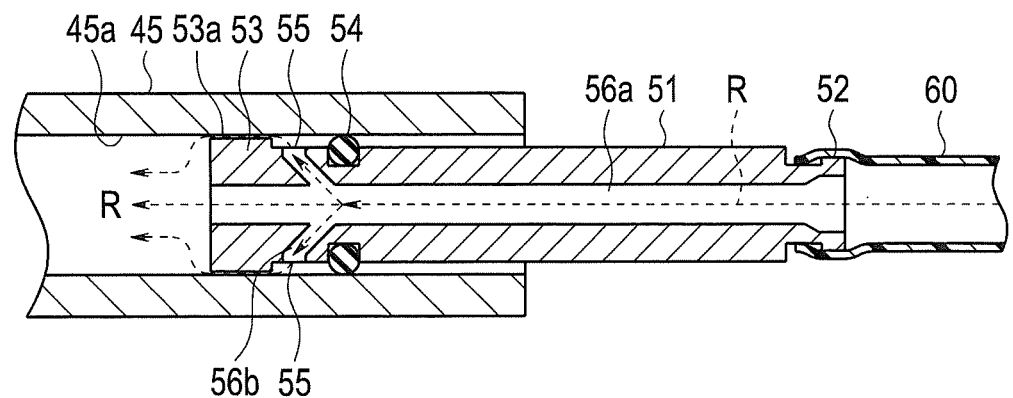
FIG. 18 is a sectional view illustrating a state in which the cleaning solution has been fed to the cylinder according to the first modification of the third embodiment.

FIGS. 17 and 18 are sectional views illustrating a state in which a cleaning solution has been fed to a cylinder according to a first modification.

Since a resistance caused when the cleaning solution is caused to flow into a clearance between the sliding surface 53a of the sliding portion 53 and the inner surface 45a of the cylinder 45 is large, a branched tubular path including a tapered surface 56c formed at a communication path 56b so as to be widened on the distal end side as illustrated in FIG. 17 may be employed, or a branched tubular path in which a communication path 56b is inclined so as to be widened on the distal end side (such that the communication path 56b is largely inclined relative to an axis that perpendicularly intersects the central axis of the piston 51) as illustrated in FIG. 18 may be employed to promote a flow of the cleaning solution R from the channel 56a to the communication path 56b.

Also, a flow of the cleaning solution R to the side of the communication path 56b may be promoted with higher priority by adjusting an opening diameter of the channel 56a and an opening diameter of the communication path 56b.

(Second Modification)

Figure 19:
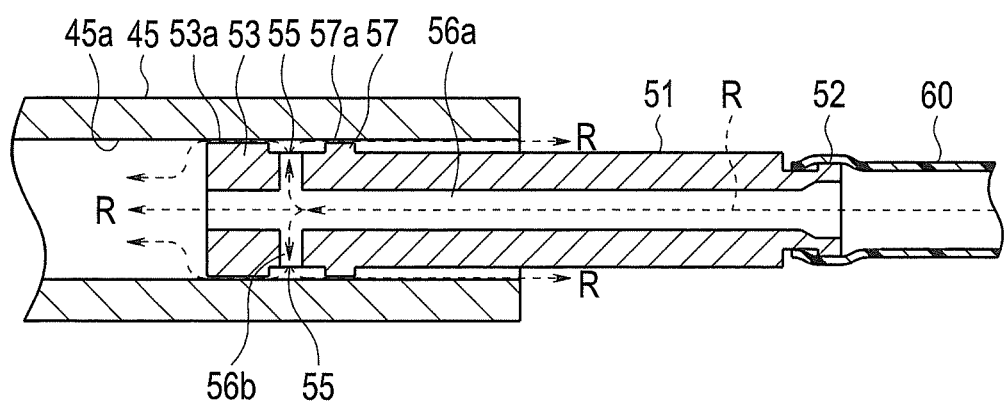
FIG. 19 is a sectional view illustrating a state in which a cleaning solution has been fed to a cylinder according to a second modification of the third embodiment.

FIG. 19 is a sectional view illustrating a state in which a cleaning solution has been fed to a cylinder according to a second modification.

As illustrated in FIG. 19, a configuration in which a sliding surface 57a of a sliding portion 57 that is separated at a predetermined distance from the sliding surface 53a of the sliding portion 53, which serves as a first contact portion on the distal end side, for example, on the proximal end side in the longitudinal axis direction is provided, and the opening portion 55 of the communication path 56b is provided between the sliding portions 53 and 57 may be employed instead of the O-shaped ring 54 that is a water-tight member that serves as a second contact portion.

In a case of such a configuration, the cleaning solution R that has been supplied to the channel 56a flows out of the opening portion 55 of the communication path 56b to the outer circumferential portion of the piston 51, cleans the sliding surface 53a of the sliding portion 53, flows to the distal end side in the cylinder 45, and also cleans the sliding surface 57a of the sliding portion 57, flows to the proximal end side of the cylinder 45, and is then discharged to the outside. The other components, effects, and advantages are the same as the components, effects, and advantages described above.

(Third Modification)

Figure 20:
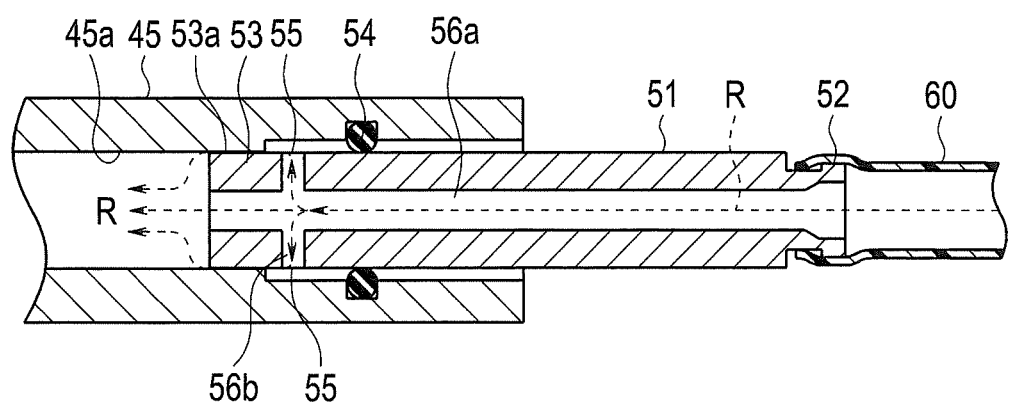
FIG. 20 is a sectional view illustrating a state in which a cleaning solution has been fed to a cylinder according to a third modification of the third embodiment.

FIG. 20 is a sectional view illustrating a state in which a cleaning solution has been fed to a cylinder according to a third modification.

The O-shaped ring 54 that is a water-tight member and serves as a second contact portion is not necessarily provided at the piston 51 and may be configured to be provided on the side of the inner surface 45a of the cylinder 45 as illustrated in FIG. 20. The other components, effects, and advantages are the same as the components, effects, and advantages described above.

Although the configuration in which the piston 51, which moves forward and backward when the raising base 42 that is provided at the distal end portion 8 of the insertion portion 5 in the endoscope 1 and that serves as a direction changing portion, is raised, to which the wire 41 is connected, is movable in the cylinder 45 has been described as an example in the aforementioned respective embodiments and the respective modifications, such a direction changing mechanism portion that serves as a piston mechanism is not necessarily used for a mechanism for raising the raising base 42.

Although targets for which the structures as illustrated in the aforementioned respective embodiments and the respective modifications, for example, are used are not limited, it is also conceivable to apply the structures to various configurations such as a configuration which is connected to a bending operation wire for bending a bending portion 9 or the like that serves as a direction changing portion, a configuration in which a wire is caused to operate an optical member at a distal end of the endoscope to change optical properties when an image is acquired, a configuration for changing hardness by causing a traction wire to be inserted into an insertion portion of the endoscope and pulling the wire, and a configuration using a wire for operating a mechanism for switching a bendable length of the aforementioned bending portion 9.

Each of the configurations in the respective embodiments and the modifications described above may be combined, and in addition, various changes can be made in an implementation stage without departing from the gist of the disclosure. Further, the aforementioned respective embodiments include inventions in various stages, and various inventions can be extracted from appropriate combinations of a plurality of configuration requirements disclosed.

Even if several configuration requirements are deleted from all the configuration requirements described in the respective embodiments, for example, the configurations from which the configuration requirements have been deleted can be extracted as the inventions as long as the aforementioned problems can be solved and the aforementioned effects can be obtained.

According to the invention, it is possible to provide an endoscope that enables easy cleaning of a sliding portion between a piston to which a wire or the like is connected and a cylinder.

What is claimed is:

1. An endoscope comprising:
    an insertion portion configured to be inserted into an object of examination from a distal end side in a longitudinal axis direction;
    a raising base provided at a distal end part of the insertion portion;
    a wire connected at one end to the raising base to move the raising base through traction and relaxation of the wire;
    a guide tube having the wire inserted in a hollow portion of the guide tube;

a piston inserted into the guide tube to move forward and backward longitudinally within the hollow portion of the guide tube, an other end of the wire being connected to the piston;

the piston having an outer circumferential surface provided on a distal end side of the piston, the outer circumferential surface being formed so as to project radially outward further than proximal portions of the piston adjacent to the outer circumferential surface such that a clearance is formed between the outer circumferential surface of the piston and a corresponding inner surface of the hollow portion of the guide tube;

a water-tight seal provided proximally relative to the outer circumferential surface, the water-tight seal being provided to seal a space between the guide tube and the piston at a longitudinal position proximal to the one or more openings;

a flow path comprising:
- a first flow path provided longitudinally inside the piston,
- a second flow path in fluid communication with a distal end of the first flow path, the second flow path extending from the distal end side of the first flow path and extending radially relative to a longitudinal axis of the piston, and
- one or more first openings formed at an end of the second flow path, the one or more first openings being arranged such that a fluid for cleaning introduced into the first flow path is directed into the clearance; and an operation member for moving the piston forward and backward longitudinally relative to the guide tube.

2. The endoscope according to claim 1, wherein the outer circumferential surface of the piston is substantially brought into surface contact with the guide tube.

3. The endoscope according to claim 1, wherein the water-tight member is provided at the piston.

4. The endoscope according to claim 1, wherein the water-tight member is provided at the guide tube.

5. The endoscope according to claim 1, wherein the one or more first openings are formed on the outer circumferential surface of the piston.

6. The endoscope according to claim 1, wherein the outer circumferential surface comprises a first outer circumferential surface and the one or more first openings are formed on a second outer circumferential surface of the piston disposed adjacent to the first outer circumferential surface.

7. The endoscope according to claim 1, wherein the second flow path is formed at substantially equal intervals around a center of the piston.

8. The endoscope according to claim 1, wherein the raising base changes a projecting direction of a treatment instrument.

9. The endoscope according to claim 1, the flow path further comprises:
a second opening at a distal end face of the piston; and
a third flow path extending from the distal end of the first flow path to the second opening.

* * * * *